United States Patent
Coleman et al.

[11] 3,977,407
[45] Aug. 31, 1976

[54] NASOTRACHEAL TUBE HOLDER

[75] Inventors: Steven J. Coleman, Marlboro; James W. O'Brien, Waltham, both of Mass.

[73] Assignee: Thermo Electron Corporation, Waltham, Mass.

[22] Filed: Sept. 3, 1974

[21] Appl. No.: 503,010

[52] U.S. Cl. .......................... 128/348; 128/DIG. 26
[51] Int. Cl.² ........................................ A61M 25/00
[58] Field of Search ............... 128/133, 206–208, 128/214 R, 215, 346–349 R, 350 R, 351, DIG. 6, DIG. 26; 24/73 AP, 73 SA, 73 SH, 81 CC; 248/74 R, 74 A, 74 B, 205 R, 205 A

[56] References Cited
UNITED STATES PATENTS

| 3,046,989 | 7/1962 | Hill | 128/206 |
|---|---|---|---|
| 3,059,645 | 10/1962 | Hasbrouck et al. | 128/133 |
| 3,146,778 | 9/1964 | Krawiec | 128/349 |
| 3,161,199 | 12/1964 | Sands | 128/348 |
| 3,288,136 | 11/1966 | Lund | 128/348 |
| 3,430,300 | 3/1969 | Doan | 128/349 R |
| 3,648,703 | 3/1972 | Manker | 128/206 |
| 3,683,911 | 8/1972 | McCormick | 128/348 |

FOREIGN PATENTS OR APPLICATIONS

| 1,184,139 | 1959 | France | 128/348 |
|---|---|---|---|
| 653,436 | 11/1937 | Germany | 128/349 |

*Primary Examiner*—John D. Yasko
*Attorney, Agent, or Firm*—James L. Neal

[57] ABSTRACT

A nasotracheal tube holder comprises a substantially straight projection having a laterally curved, trough-like surface mounted on a base for securing said projection to a person's head such that the projection is adapted to receive in longitudinally aligned relation the protruding end of a nasotracheal tube in its applied working position. In a preferred embodiment a pair of laterally opposed tabs at the outer end of the projection serve as stop lugs for preventing a wrapping, such as tape, which binds the tube to the projection from sliding off the projection.

1 Claim, 3 Drawing Figures

NASOTRACHEAL TUBE HOLDER

CROSS-REFERENCE TO RELATED APPLICATION

The subject matter of this application is related to application Ser. No. 502,692, filed Sept. 3, 1974.

BACKGROUND OF THE INVENTION

The present invention relates generally to the art of positioning and securing an endotracheal tube for conducting air, oxygen or oxygen and an anesthetic gas mixture. It is well known to those skilled in the art that means may be inserted in a person's mouth to support an oral endotracheal tube. However, endotracheal tubes are inserted through the nose, such tubes being called nasotracheal tubes.

It is an object of the present invention to provide a nasotracheal tube holder having means for mounting a nasotracheal tube securely and easily and which inhibits axial movement of such a tube.

SUMMARY OF THE INVENTION

The invention described herein is a nasotracheal tube holder having an elongated, shallow trough-like projection adapted to receive in longitudinally aligned relation the outside surface of a nasotracheal tube. The projection can easily and securely mount the tube by tape or other means. The projection is connected to a plastic strip for mounting it on the face of a patient just beneath the nasal opening in approximate alignment with the protruding end of a nasotracheal tube in its applied working position. In a preferred embodiment the projection has protruding tabs at its end to block the tape or other similar means so that it does not slide off.

DETAILED DESCRIPTION OF THE DRAWINGS

Figure 1:
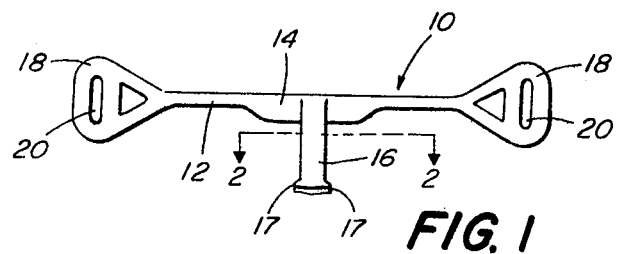
FIG. 1 is a frontal elevation of one embodiment of the present invention.
Figure 2:
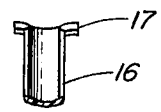
FIG. 2 is a cross section taken along line 2—2 in FIG. 1.
Figure 3:
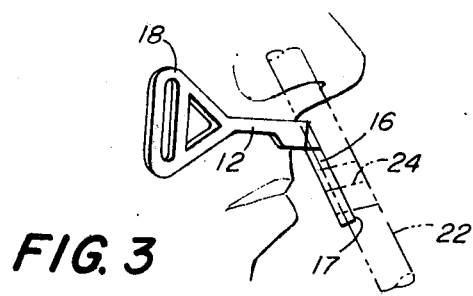
FIG. 3 is a side elevation of the invention shown in FIG. 1 as applied in service position.

A preferred embodiment of the present invention is shown in FIGS. 1, 2 and 3. A nasotracheal tube holder 10 comprises an elongated, flattened strip of suitable plastic material 12 of sufficient flexibility to conform to the contour of the front of the face beneath the nasal opening. At its center the strip is widened, forming a flat base 14 on which is mounted an elongated projection 16. The flat base is configured to lie beneath the nasal opening and above the upper lip. The projection is laterally curved along its length, thus forming a shallow trough. The curvature of the trough is similar to that of typical outside radii of nasotracheal tubes to facilitate mounting of such a tube upon the projection. The projection is sufficiently narrow that the tube lays upon it as upon a supporting platform rather than mating with it as with a circumscribing sleeve or partial sleeve. The curve of the projection contacts the tube along an arc substantially less than 180° in extent. Two opposing tabs 17 protrude from opposite sides of the projection at its outer end to serve as stop lugs. The projection is integral with the widened center portion of the strip 14 and extends downward from it at an acute angle to it so that the projection is approximately aligned with the nasal passage when the elongated, flattened strip is in its applied working position. As shown in FIG. 3, means 18 at each end of the strip lie on opposite cheeks and form slots 20, each adapted to receive one end of an adjustable band, not shown. The band is inserted through the slots 20 in the ends of the frame, passed around the head and tightened. This anchors the tube holder firmly in place. An adjustable cloth band is preferred to provide a firm attachment of the holder without the excessive pressure sometimes caused by an elastic strap.

In use, the nasal tube holder 10 is placed so that a flat surface of the strip 12 contacts the face and the projection 16 is aligned with one of the nasal openings. The holder is then secured to the head by tightening the band. This can be done either before or after the patient has been intubated with a nasotracheal tube 22. After intubation, the protruding end of the tube is aligned axially with the projection, and fastening means such as tape 24 is wrapped around both the projection and tube to bind them tightly together. Adhesive tape is a suitable fastening means because it is commonly available in hospitals where a nasotracheal tube would be used and it offers a quick, convenient and inexpensive means of attachment. Moreover, it provides an adhesive force and does not tend to close off the tube. Similar advantages accrue from suturing the tube to the projection 16.

When tape is used it tends to become moist during extended use. Good securing contact between the fastening means and the projection tends to be difficult to achieve because the bond between the fastening means and the tube holder can loosen and cause the fastening means to slide. However, according to the preferred embodiment of the present invention, the tape will engage the protruding tabs 17 and its movement will be prevented. This, in turn, inhibits any further movement of the endotracheal tube.

We claim:

1. A one-piece holder for securing a nasotracheal tube in its applied working position comprising an elongated, flattened strip of a width not greater than the space between the nasal opening and the upper lip for lying on the face of a subject just beneath the nasal opening having an integrally formed elongated projection extending from a central portion thereof at an acute angle with respect thereto to align said projection with a nasal passage of a subject when the holder is in its working position and means adjacent each end of said strip adapted to lie on opposite cheeks of the subject for attaching to a head encircling band, said projection forming a shallow trough therealong for mounting such nasotracheal tube in longitudinal alignment therewith, said projection being adapted to receive an adhesive binding means wrapped around both such nasotracheal tube and said projection to firmly bind together said projection and such tube, and tab means extending from the end of said projection for inhibiting any tendency of said binding means to slide off said projection.

* * * * *